United States Patent [19]
Nichols

[11] Patent Number: 6,050,992
[45] Date of Patent: Apr. 18, 2000

[54] APPARATUS AND METHOD FOR TREATING TISSUE WITH MULTIPLE ELECTRODES

[75] Inventor: Colin J. Nichols, Fremont, Calif.

[73] Assignee: Radiotherapeutics Corporation, Sunnyvale, Calif.

[21] Appl. No.: 08/858,414

[22] Filed: May 19, 1997

[51] Int. Cl.⁷ .................................................. A61B 18/14
[52] U.S. Cl. ............................... 606/41; 606/49; 606/50; 607/99; 607/113; 607/116
[58] Field of Search .................. 606/41, 49, 50, 606/129; 607/98, 99, 113, 116, 122, 128; 600/505, 375, 376

[56] References Cited

U.S. PATENT DOCUMENTS

| | | | |
|---|---|---|---|
| 3,347,224 | 10/1967 | Adams | 600/505 |
| 5,237,996 | 8/1993 | Waldman et al. | 600/374 |
| 5,507,802 | 4/1996 | Imran . | |
| 5,536,267 | 7/1996 | Edwards et al. . | |
| 5,683,384 | 11/1997 | Gough et al. . | |
| 5,868,740 | 2/1999 | LeVeen et al. | 606/41 |

FOREIGN PATENT DOCUMENTS

WO 96/29946   10/1996   WIPO .

*Primary Examiner*—Lee Cohen
*Attorney, Agent, or Firm*—Townsend and Townsend and Crew LLP

[57] ABSTRACT

A probe system for volumetric tissue heating and ablation comprises a cannula having a multiple electrode component reciprocatably mounted therein. Individual electrodes within the array have spring memory so that they assume a radially outward, arcuate configuration as they are advanced distally from the cannula. Preferably, the electrodes fully evert as they are advanced from the cannula. Prior to deployment, the electrodes are constrained within a lumen of the cannula. The electrodes are maintained with a uniform circumferential spacing by confining them within an annular envelope defined by a core member within the cannula lumen, by providing electrodes having asymmetric cross-sectional geometries, and/or by nesting the electrodes closely together. Optionally, a cutting current may be applied to the electrodes as they are advanced.

66 Claims, 10 Drawing Sheets

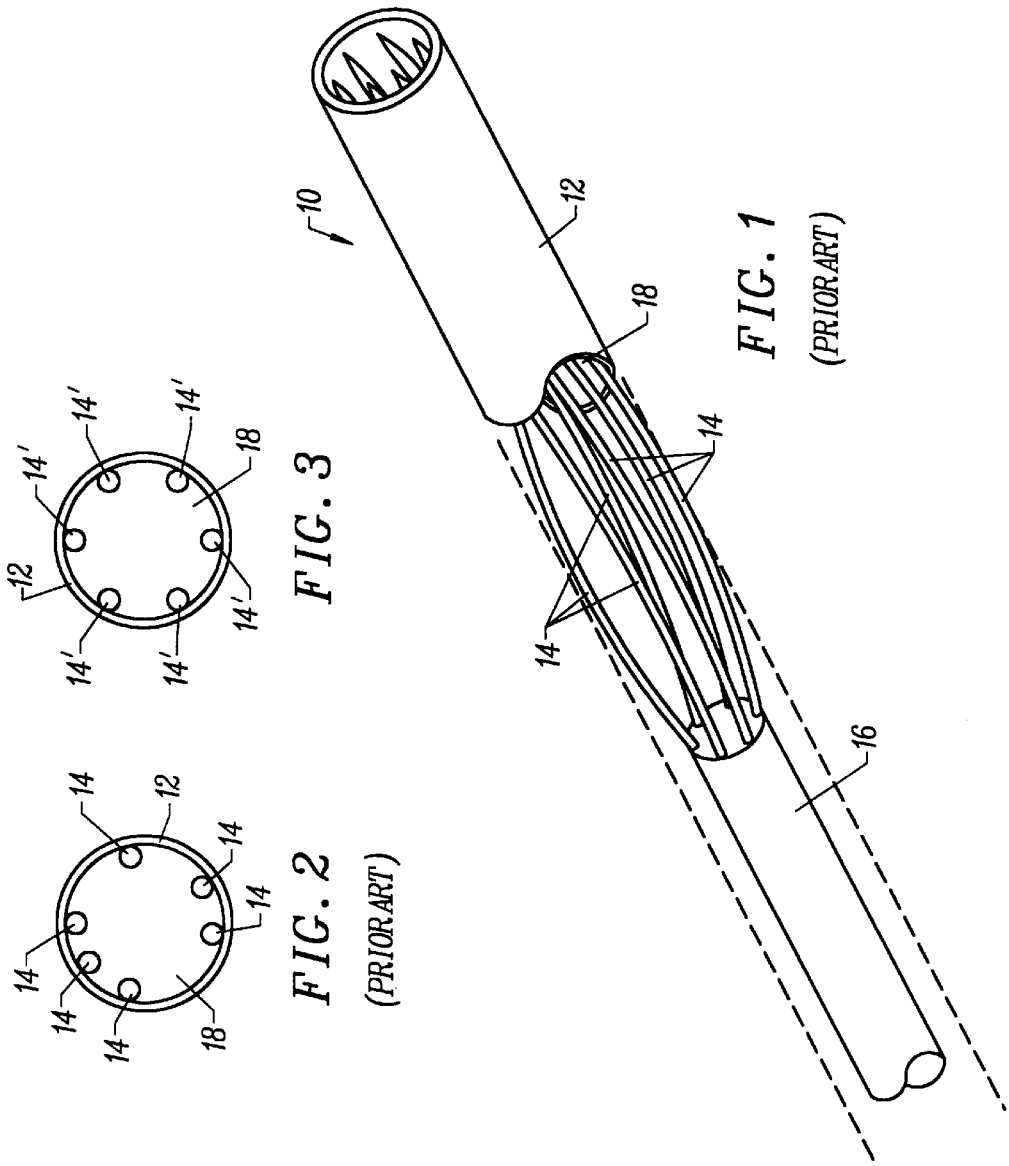

APPARATUS AND METHOD FOR TREATING TISSUE WITH MULTIPLE ELECTRODES

BACKGROUND OF THE INVENTION

The present invention relates generally to the structure and use of radio frequency electrosurgical probes for the treatment of solid tissue. More particularly, the present invention relates to an electrosurgical probe having multiple tissue-penetrating electrodes which are deployed in an array to treat large volumes of tissue, particularly for tumor treatment.

The delivery of radio frequency energy to target regions within solid tissue is known for a variety of purposes of particular interest to the present invention, radio frequency energy may be delivered to diseased regions in target tissue for the purpose of tissue necrosis. For example, the liver is a common depository for metastases of many primary cancers, such as cancers of the stomach, bowel, pancreas, kidney and lung. Electrosurgical probes for deploying multiple electrodes have been designed for the treatment and necrosis of tumors in the liver and other solid tissues. See, for example, the electrosurgical probe described in published PCT application WO 96/29946.

The probes described in WO 96/29946 comprise a number of independent wire electrodes which are extended into tissue from the distal end of a cannula. The wire electrodes may then be energized in a monopolar or bipolar fashion to heat and necrose tissue within a precisely defined volumetric region of target tissue. In order to assure that the target tissue is adequately treated and limit damage to adjacent healthy tissues, it is desirable that the array formed by the wire electrodes within the tissue be precisely and uniformly defined. In particular, it is desirable that the independent wire electrodes be evenly and symmetrically spaced-apart so that heat is generated uniformly within the desired target tissue volume. Such uniform placement of the wire electrodes is difficult to achieve when the target tissue volume has non-uniform characteristics, such as density, tissue type, structure, and other discontinuities which could deflect the path of a needle as it is advanced through the tissue.

Referring now to FIGS. 1–5, a shortcoming of electrosurgical probes of the type described in WO 96/29946 will be discussed. Such electrosurgical probes 10 typically comprise a cannula 12 having a plurality of resilient, pre-shaped electrodes 14 therein. The electrodes 14 may be mounted at the distal end of a reciprocatable shaft 16, and the electrodes 14 will be shaped so that they assume an arcuate shape to produce an everting array when the electrodes are advanced from the cannula 12 into solid tissue, as illustrated in FIGS. 4 and 5. With prior electrode probes, such as the illustrated probe 12, the electrodes 14 have been received within lumen 18 of the cannula 12. The electrodes have had circular cross-sections, and no provisions have been made to maintain the individual electrodes 14 in any particular ordered fashion within the cannula. Usually, a random pattern of electrodes 14 exist within the cannula 12, as shown in FIGS. 1 and 2. When electrodes 14 are initially present in such a random pattern (i.e. prior to distal deployment into tissue), the electrodes will adopt a similar random pattern or configuration when first entering into tissue T. When the electrode pattern is non-uniform at the time of first entering into tissue, the non-uniformity will be propagated as the electrodes are fully deployed, as illustrated in FIG. 4. Such a random, irregular pattern is undesirable since it results in non-uniform heating and tissue necrosis.

It would be desirable to provide improved electrosurgical probes of the type described in WO 96/29946, where the individual electrodes 14' are maintained in a uniform pattern within the cannula 12, as illustrated in FIG. 3. In particular, the electrodes 14' should be equally circumferentially spaced-apart and preferably axially aligned with each other within the cannula so that they will follow uniform, equally spaced-apart lines of travel as they penetrate into tissue, as shown in FIG. 5. It will be appreciated that the initial point at which the electrodes penetrate tissue is critical to maintain proper spacing of the electrodes as they penetrate further into the tissue. Should electrodes be misaligned when they first enter the target (i.e. emerge from the cannula) tissue, they will almost certainly remain misaligned as they penetrate further into the tissue. Moreover, the individual electrodes will generally not be steerable or capable of being redirected within the tissue, so there are few options for correcting the configuration after the needles have first penetrated into the tissue. In contrast, by properly aligning the electrodes prior to and at the time they first enter into tissue from the cannula, the proper electrode pattern can be assured as the electrodes deploy radially outwardly into the tissue. It would be still further desirable to provide electrosurgical probes and methods for their deployment which would provide for improved propagation through tissue having non-uniform characteristics. Even when the electrodes are disposed in a symmetrical pattern at the outset of deployment, the electrode paths can be deflected or deviated when the electrodes encounter relatively hard or dense regions within the tissue. It would be beneficial if the electrodes were capable of passing through such regions with minimum or no deflection.

For these reasons, it would be desirable to provide improved electrosurgical probes having multiple, tissue-penetrating electrodes. In particular, it would be desirable to provide improved electrosurgical probes and tissue ablation apparatus of the type described in WO 96/29946, where the electrodes are configured within the probes so that they deploy in a uniform, evenly spaced-apart manner as they penetrate into tissue to be treated, thus overcoming at least some of the shortcomings noted above.

SUMMARY OF THE INVENTION

The present invention provides both apparatus and methods for the electrical treatment of a specific region within solid tissue, referred to hereinafter as a "treatment region." The apparatus and methods rely on introducing a plurality of electrodes, usually being at least three electrodes, to a target site within the treatment region and thereafter deploying the electrodes into a three-dimensional array and preferably in a configuration which conforms to or encompasses the entire volume of the treatment region, or as large a portion of the volume of the treatment region as possible. The present invention particularly provides for uniform deployment of the electrodes within the solid tissue. By "uniform deployment," it is meant that adjacent electrodes are evenly spaced-apart from each other and that pairs of adjacent electrodes are spaced-apart in a repeating, uniform pattern so that the application of electrical current through the electrodes will result in generally uniform heating and necrosis of the entire tissue volume being treated. Usually, the treatment current is radio frequency (RF) current which may be applied to the tissue in a monopolar or bipolar fashion, as described in more detail below.

Apparatus according to the present invention comprises a probe system for penetrating a plurality of electrodes into tissue. The probe system includes a cannula having a proximal end, a distal end, and a lumen extending at least to the distal end, and usually from the proximal end to the distal end. The individual electrodes are resilient and pre-shaped to assume a desired configuration when advanced into tissue. Usually, the individual electrodes will have an arcuate shape (when unconstrained) so that the electrode arrays deploy radially outwardly as the electrodes are advanced distally from the probe. In a particularly preferred configuration, the electrode arrays are "everting" where the electrode tips first diverge radially outwardly and thereafter turn by more than 90°, often to 180°, or more, in the proximal direction. The deployed electrodes will usually define a generally cylindrical, conical, or spherical volume having a periphery with a maximum radius in the range from 0.5 to 3 cm.

The apparatus of the present invention maintains at least the distal tips of the individual electrodes within the cannula lumen with a substantially equal circumferential spacing therebetween with an annulus or annular envelope near the distal end of the cannula lumen. Usually, the spacing between adjacent electrodes at the distal tip of the cannula will vary by less than ±10%, preferably being less than ±5%, of the average spacing (i.e., total circumferential distance divided by the number of circumferentially deployed electrodes). Preferably, the electrodes will be maintained generally parallel to each other in the axial direction so that the initial entry of the electrodes into the tissue and subsequent passage of the electrodes through the tissue will be in substantially similar patterns (although in circumferentially spaced-apart directions). The annulus can be defined in a variety of ways, as described below.

In a first particular aspect of the present invention, the probe system comprises a core disposed coaxially within the cannula lumen to maintain substantially equal circumferential spacing between the electrodes when retracted in the cannula lumen. The core has a cylindrical outer surface which together with an inner surface of the cannula lumen defines the annulus or annular envelope for holding the electrodes. The annular envelope will preferably have a width in the radial direction which is less than or equal to twice the thickness of the electrodes, more preferably being less than or equal to 1.5 times the thickness. By limiting the width thusly, the electrodes will not be able to pass over each other and become misaligned while they are present in the annular envelope of the cannula. In the case of electrodes having unequal thickness, it will be necessary to limit the width to no more than the combined thicknesses of the two smallest adjacent electrodes to assure that adjacent electrodes cannot pass over each other. The electrodes, which are usually shaped to assume an arcuate configuration, are thus constrained within the annular envelope and held in a generally evenly spaced-apart manner. It has been found provision of such a core within the electrodes greatly increases the uniformity of penetration into tissue when compared to identical electrodes in the absence of a core in the cannula lumen.

The cannula core may be mechanically coupled to and reciprocate with the electrodes. In such case, it is desirable that the core have a sharpened distal end so that it can penetrate into tissue at the same time the electrodes penetrate into tissue. The core may be electrically coupled to the electrodes (in which case it acts as an additional electrode), or may be electrically isolated from the electrodes. It is possible that the core could act as a common or counter electrode in operating the probe in a bipolar manner. In a specific example, either the outer cylindrical surface of the core, the inner surface of the cannula, or both, may have axial channels formed therein for receiving and axially aligning the individual electrodes as the electrodes are advanced from the probe.

In a second particular aspect, the probe system comprises electrodes having asymmetric cross-sections with a major dimension aligned circumferentially and a minor dimension aligned radially. Usually, the major dimension will be at least 50% greater than the minor dimension, with such electrodes typically having a rectangular or trapezoidal cross-section. Electrodes having such cross-sectional dimensions are generally stiffer in the transverse direction and more flexible in the radial direction. By increasing transverse stiffness, proper circumferential alignment of the electrodes within an annulus within the open cannula lumen is enhanced. Exemplary electrodes will have a width (in the circumferential direction) in the range from 0.6 mm to 0.2 mm, preferably from 0.4 mm to 0.35 mm, and a thickness (in the radial direction) in the range from 0.05 mm to 0.3 mm, preferably from 0.1 mm to 0.2 mm. Often, the use of asymmetric electrodes will be sufficient in itself to provide for uniform electrode deployment, but in some instances it may be desirable to combine asymmetric electrode design with the use of a core and/or annular electrode envelope to maximize proper electrode alignment within the cannula.

In a third particular aspect of the apparatus of the present application, the electrodes may be closely packed or "nested" within an annular electrode envelope within the lumen of the cannula. Usually, although not necessarily, such nested electrodes will have an asymmetric cross-section, as generally described above. By nesting the electrodes, uniform deployment of the electrode tips from the distal end of the cannula is assured. The use of nested electrodes may be combined with a cannula core, as described above. When the electrodes are nested, it will often be sufficient to extend the core only within the proximal portion of the cannula, leaving the distal core region empty and without structure. The absence of the core near the distal end of the cannula can be beneficial as it can facilitate electrode retraction back into the cannula, avoiding jamming caused by tissue trying to reenter a restricted annular envelope defined by the core within the cannula.

According to the method of the present invention, plurality of at least three electrodes is constrained within the cannula. The electrodes have distal tips arranged in a substantially equally spaced-apart pattern within an annular region near the distal end of the cannula. The annular region may be provided by any of the structures described above. The electrodes are advanced distally from the cannula into tissue at a target region within the tissue. By properly aligning the electrodes within the cannula, the electrodes deploy radially outwardly in a symmetric pattern into the tissue. The tissue is then treated by applying electrical current to the electrodes, typically radio frequency current, in a monopolar or bipolar fashion.

The annulus within the cannula may be defined between an outer cylindrical surface of a core member and an inner cylindrical surface of a cannula lumen. In such cases, the core member may be advanced into the tissue together with the electrodes or may be maintained stationary within the cannula as electrodes are advanced. Preferably, the electrodes have an asymmetric cross-section with a major dimension aligned circumferentially within the annular envelope and a minor dimension aligned radially within the annular envelope. Such electrodes are pre-shaped to bend about an axis parallel to the major dimension as the electrodes are advanced distally from the cannula into tissue, resulting in the preferred everting electrode array of the present invention.

Alternatively, the annulus within the cannula may be defined by nesting the electrodes in a closely packed pattern so that the desired alignment is maintained within the cannula lumen. Preferably, the electrodes are nested over at least 50% of their lengths, more preferably over 75% of their lengths, so that axial alignment of the adjacent electrodes is achieved.

In another aspect of the method of the present invention, electrodes are deployed in tissue by providing a plurality of at least three electrodes constrained within a cannula. Each of the electrodes is then advanced distally from the cannula into tissue, and spacing between adjacent electrodes is maintained to within ±20% of the average distance between electrodes at all times while the electrodes are advanced. Preferably, the spacing is maintained to within ±10% of the average distance, and more preferably to within ±5% of the average distance. Such uniform advancement of the electrodes may be achieved by any of the apparatus and methods described above.

In a still further aspect of the method of the present invention, electrodes are deployed into tissue by disposing at least two electrodes at a target site in or on the tissue. The electrodes are then advanced into the tissue while applying a RF current to the tissue through the electrodes. The RF current will be selected to have a voltage, power, and waveform which facilitate passage of the electrodes through the tissue by reducing resistance to electrode advancement. The application of a "deployment" current to the electrodes can be used as an alternative to or in addition to sharpening of the distal tips of the electrodes to facilitate passage through tissue. After the electrodes are deployed in a uniform manner, as described above, an "ablation" current can be applied through the electrodes to treat the tissue. Suitable deployment currents will have a voltage in the range from 50 V to 200 V (peak-to-peak), usually from 50 V to 100 V, and a power in the range from 100 W to 300 W, usually from 100 W to 200 W. The waveform is not critical. Suitable ablation currents will have a voltage below 150 V (peak-to-peak), usually being from 50 V to 100 V. The power will usually be from 40 W to 100 W with a sine wave form.

BRIEF DESCRIPTION OF THE DRAWINGS

FIGS. 1–5 illustrate the prior art and objectives of the present invention, as discussed in the Background section hereinabove.

DESCRIPTION OF THE SPECIFIC EMBODIMENTS

Figure 4:
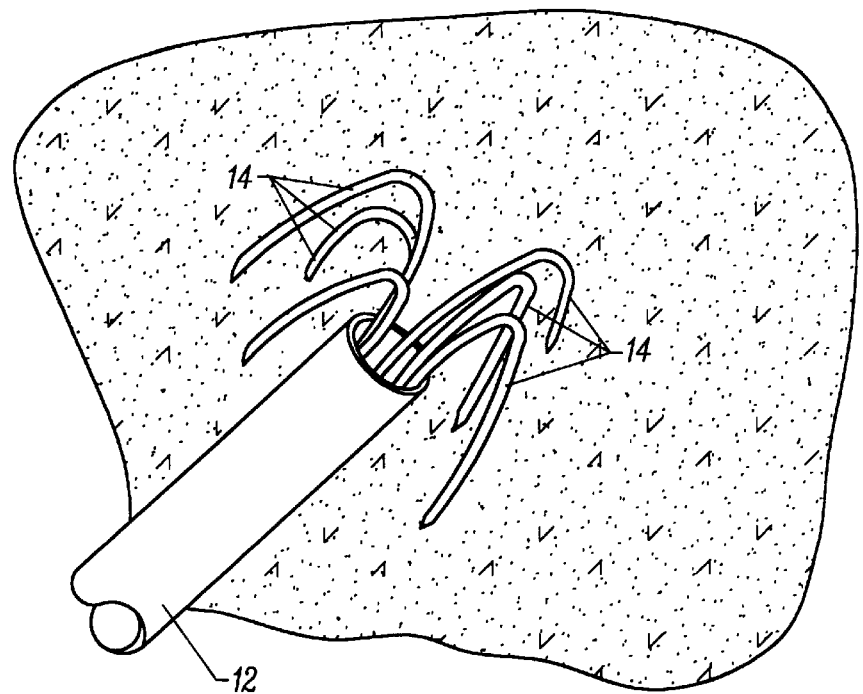
Figure 5:
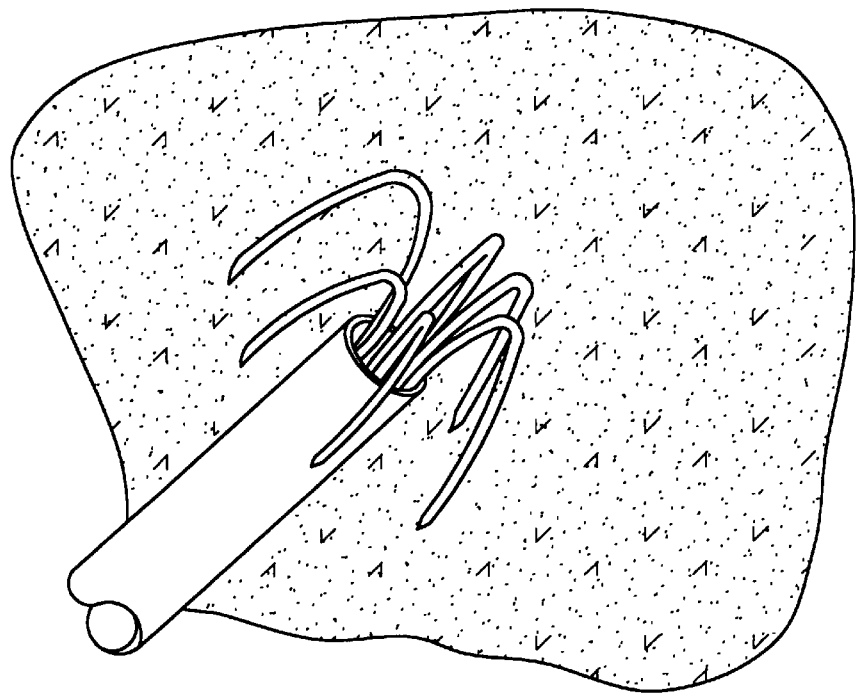

Systems according to the present invention will be designed to introduce a plurality of electrode elements to a treatment region within solid tissue of a patient. The treatment region may be located anywhere in the body where hyperthermic exposure may be beneficial. Most commonly, the treatment region will comprise a solid tumor within an organ of the body, such as the liver, kidney, pancreas, breast, prostate (not accessed via the urethra), and the like. The volume to be treated will depend on the size of the tumor or other lesion, typically having a total volume from 1 cm$^3$ to 150 cm$^3$, usually from 1 cm$^3$ to 50 cm$^3$, and often from 2 cm$^2$ to 35 cm$^2$. The peripheral dimensions of the treatment region will usually be regular, e.g. spherical or ellipsoidal, but will more usually be irregular. The treatment region may be identified using conventional imaging techniques capable of elucidating a target tissue, e.g. tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound which can be employed to monitor the size and location of the tumor or other lesion being treated, either intraoperatively or externally.

Systems according to the present invention will employ a plurality of tissue-penetrating electrodes, typically in the form of sharpened, small diameter metal elements which can penetrate into tissue as they are advanced from a target site within the target region, as described in more detail hereinafter. The primary requirement of such electrode elements is that they can be deployed in an array, preferably a three-dimensional array, emanating generally from a target site within the treatment region of the tissue. The electrode elements will be first introduced to the target site in a radially collapsed or other constrained configuration, and thereafter advanced into the tissue from a delivery cannula or other element in a divergent pattern to achieve the desired three-dimensional array. The electrode elements will diverge radially outwardly from the delivery cannula (located at the target site) in a uniform pattern, i.e. with the spacing between adjacent electrodes diverging in a substantially uniform and/or symmetric pattern. In the exemplary embodiments, pairs of adjacent electrodes will be spaced-apart from each other in similar or identical, repeated patterns and will usually be symmetrically positioned about an axis of the delivery element. The electrode elements may extend or project along generally straight lines from the target site, but will more usually be shaped to curve radially outwardly and optionally to evert proximally so that they face partially or fully in the proximal direction when fully deployed. It will be appreciated that a wide variety of particular patterns can be provided to uniformly cover the region to be treated.

A preferred form of the individual electrode element of an electrode array is a single wire having a shaped distal portion which can be extended from the delivery cannula or other element at the target site in the tissue to diverge in a desired pattern. Such wires can be formed from conductive metals having a suitable shape memory, such as stainless steel, nickel-titanium alloys, nickel-chromium alloys, spring steel alloys, and the like. The wires may have circular or non-circular cross-sections, preferably having asymmetrical cross-sectional shapes as discussed in detail below. Optionally, the distal ends of the wires may be honed or sharpened to facilitate their ability to penetrate tissue. The distal ends of such wires may be hardened using conventional heat treatment or other metallurgical processes. Such wires may be partially covered with insulation, although they will be at least partially free from insulation over their distal portions which will penetrate into the tissue to be treated. In the case of bipolar electrode arrays, it will be necessary to insulate the positive and negative electrode wires in any regions where they would or could be in contact with each other during the power delivery phase. In the case of monopolar arrays, it may be possible to bundle the wires together with their proximal portions having only a single layer of insulation over the entire bundle. Such bundled wires may be brought out directly to a suitable RF power supply, or may alternatively be connected via other (intermediate) electrical conductors, such as coaxial cable, or the like.

The above described electrode characteristics apply only to active electrodes intended to have the desired surgical effect, i.e. heating of the surrounding tissue. It will be appreciated that in monopolar operation, a passive or dispersive "electrode" must also be provided to complete the return path for the circuit being created. Such electrodes, which will usually be attached externally to the patient's skin, will have a much larger area, typically about 130 $cm^2$ for an adult, so that current flux is sufficiently low to avoid significant heating and other biological effects. It may also be possible to provide such a dispersive return electrode directly on a portion of a sheath, core element, or other portion of the system of the present invention, as described in more detail below (generally, when the return electrode is on the sheath or core, the device will still be referred to as bipolar).

The RF power supply may be a conventional general purpose electrosurgical power supply operating at a frequency in the range from 300 kHz to 1.2 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for the methods of the present invention. Thus, such power supplies will usually be operated at the lower ends of their voltage and power capabilities. More suitable power supplies will be capable of supplying an ablation current at a relatively low voltage, typically below 150 V (peak-to-peak), usually being from 50 V to 100 V. The power will usually be from 50 W to 150 W, usually having a sine wave form, but other wave forms would also be acceptable. Power supplies capable of operating within these ranges are available from commercial vendors, such as Radionics and RadioTherapeutics Corporation A preferred power supply is model RF-2000, available from Radio-Therapeutics Corporation, Mountain View, Calif., assignee of the present application.

In addition to providing ablation current, the power supplies of the present invention may also be used for providing a deployment current to the electrodes to facilitate advancement of the electrodes through tissue, typically prior to delivery of the ablation current. Suitable deployment currents will not necessarily be different from the ablation currents, typically having a voltage in the range from 50 V to 200 V (peak-to-peak), usually from 50 V to 100 V and a power in the range from 100 W to 300 W, usually from 100 W to 200 W. The wave form of the ablation current is not critical, and can be either a "ringing" wave form typical of electrosurgical coagulation, or a sine wave form, typical of electrosurgical cutting. The application of a deployment current during the advancement of the electrodes will be particularly beneficial during the initial stages of advancement. As the electrode extends further into tissue, the concentration of the current flux at the tip of the electrode will be dissipated, and will therefore have less of a "cutting" effect as the electrode is advanced. Fortunately, however, proper deployment of the electrodes at the earliest stages of their advancement is most critical. Thus, application of a deployment current to the electrodes in order to permit proper orientation of the electrodes at the outset can be achieved.

The plurality of electrode elements will usually be contained by or within an elongate member, typically a rigid or semi-rigid, metal or plastic cannula. In some cases, the cannula will have a sharpened tip, e.g. be in the form of a needle, to facilitate introduction to the tissue target site. In such cases, it is desirable that the cannula or needle be sufficiently rigid, i.e. have sufficient column strength, so that it can be accurately advanced through tissue. In other cases, the cannula may be introduced using an internal stylet which is subsequently exchanged for the electrode array. In the latter case, the cannula can be relatively flexible since the initial column strength will be provided by the stylet. The cannula serves to constrain the individual electrode elements in a radially collapsed configuration to facilitate their introduction to the tissue target site . The electrode elements can then be deployed to their desired configuration, usually a three-dimensional configuration, by extending distal ends of the electrode elements from the distal end of the cannula into the tissue. In the preferred case of the tubular cannula, this can be accomplished simply by advancing the distal ends of the electrode elements distally from the tube so that they emerge and deflect (usually as a result of their own spring or shape memory) in a radially outward pattern. Alternatively, some deflection element or mechanism could be provided on the elongate member to deflect members with or without shape memory in a desired three-dimensional pattern.

A component or element may be provided for introducing the cannula to the target site within the treatment region to be treated. For example, a conventional sheath and sharpened obturator (stylet) assembly can be used to initially access the target site. The assembly can be positioned under ultrasonic or other conventional imaging, with the obturator/stylet then being removed to leave an access lumen through the sheath. The electrode elements can then be introduced through the sheath lumen, typically while constrained in the cannula. Alternatively, the cannula may have a sharpened distal tip and/or an electrode tip to facilitate initial introduction to the tissue target site. Application of cutting RF current through an electrode on the cannula tip will facilitate penetration through tissue in a conventional manner. In such cases, the electrodes may be disposed within the cannula lumen while the cannula is being placed. When the cannula is electrically conductive, e.g. composed of a metal, appropriate insulation will have to be provided on the interior and/or exterior of the cannula to prevent unintended conduction of the RF energy being applied through the electrodes. In some instances, the cannula may be insulated from the deployed electrodes but have an exterior surface configured to provide a common or ground electrode for bipolar operation.

After the cannula is properly placed, the electrode elements are extended distally beyond the distal end of the cannula into the treatment region of tissue, and the cannula can subsequently be withdrawn or left in place. RF current can then be applied through the electrodes in either a monopolar or bipolar fashion. With monopolar treatment, a dispersive plate attached externally to the patient is attached to the other lead from the RF power supply. Alternatively, a return electrode having a relatively large surface area can be provided on the cannula. In bipolar operation, the individual electrode elements can be connected alternately to the two poles of the RF power supply. Alternatively, one or more additional electrode elements can be penetrated into the tissue and serve as a common, second polar electrode.

The probe systems of the present invention will comprise a plurality of electrodes. While in some instances the plurality may include as few as two electrodes, usually the plurality will include at least three electrodes, more usually including at least five electrodes, preferably including at least eight electrodes, and more preferably including at least ten electrodes. Probe systems comprising twelve, fourteen, sixteen, eighteen, or even twenty individual electrodes will also find use.

The cannula and electrode wires of the present invention may be formed separately and be separable from each other. Usually, both the cannula and the electrode wires will be packaged and/or assembled together in a single sterile package and intended to be used together. Frequently, both the cannula and the accompanying electrode component will be disposable. Alternatively, any or all of the components of the assembly may be sterilizable and reusable, at least for a limited number of reuses. optionally, the cannula and electrode components may be packaged and maintained separately, typically in sterile packaging. Thus, when referred to as a system, it is contemplated that the cannula and electrode components of the system may be made available separately and later combined by a user into a single system.

Although typically introduced through a previously formed tissue penetration, the probe and cannula of the present application may be adapted to be self-penetrating. That is, the cannula may include a sharpened distal end which may be introduced directly into tissue. Alternatively, a separate sheath may be introduced with a separate stylet, and the stylet then removed for exchange with an assembly including the cannula and electrode wires of the system of the present invention. Other particular systems and methods for introducing the probe system may also be developed within the scope of the present invention.

The features of the probe system described thus far are generally similar to those of the probe system described in WO 96/29946, which is also pending as U.S. Ser. No. 08/410,344, the full disclosure of which is incorporated herein by reference. Although the probe system described therein preferably results in a uniform and symmetric electrode array within tissue, the ability to achieve such a uniform array is limited for the reasons described hereinabove. The probe system of the present invention, in contrast, provides particular structural features which enhance uniformity of electrode arrays as the individual electrodes are advanced into tissue from the cannula. A first such structural feature comprises a core element disposed coaxially within the cannula lumen which accommodates the individual electrodes. The core element is preferably a cylindrical (or tubular) body having an outer cylindrical surface which together with an inner cylindrical surface of the lumen defines an annular envelope for receiving and constraining the electrode elements. The electrode elements, which preferably have an arcuate spring memory, will be constrained within the annular envelope and held in a uniformly spaced-apart and axially parallel configuration. It has been found that electrodes advanced from such a uniform initial condition will advance symmetrically and uniformly into the solid tissue of the target region.

A second structural feature of the present invention which enhances electrode deployment uniformity is provided by the cross-sectional shape of the individual electrodes. Preferably, the individual electrodes have an asymmetric cross-section with a major dimension aligned circumferentially within the cannula and a minor dimension aligned radially within the cannula lumen. Usually, the major dimension is at least 50% greater than the minor dimension, and the enhanced "Iwidth" of the individual electrodes helps assure that they remain axially aligned and evenly spaced-apart circumferentially within the cannula lumen. In the most preferred embodiments, both the annular envelope and asymmetric electrode design will be employed to maximize proper electrode alignment and uniformity of deployment.

A third structural feature of the present invention which enhances electrode deployment uniformity is provided by nesting or closely packing the adjacent electrodes within an annulus about the interior lumen of the cannula. By "nesting" it is meant that the adjacent electrodes lie in contact with each other, or within a very close distance, so that the adjacent electrode elements come into contact and self-align as they are retracted into the cannula lumen. In a specific example, the electrode elements may have trapezoidal cross-sections, as illustrated in the specific embodiments hereinafter. Such a trapezoidal cross-section, however, is not necessary, and the electrodes could have square, circular, rectangular, or even non-uniform cross-sections so long as they are closely packed and fall into alignment as the electrodes are drawn back into the cannula lumen.

It will be appreciated that any one of these structural features may be employed by itself or together with one or both of the other structural features to achieve the electrode alignment feature of the present invention. For example, it will frequently be desirable to provide nested electrodes having asymmetric cross-sections to cause the electrodes to lie within the desired annulus near the distal end of the cannula lumen. Such nested, asymmetric electrodes may further be combined with a core element which extends partially or totally through the lumen of the cannula, where the core element could be moveable or stationary relative to the cannula.

Figure 6:
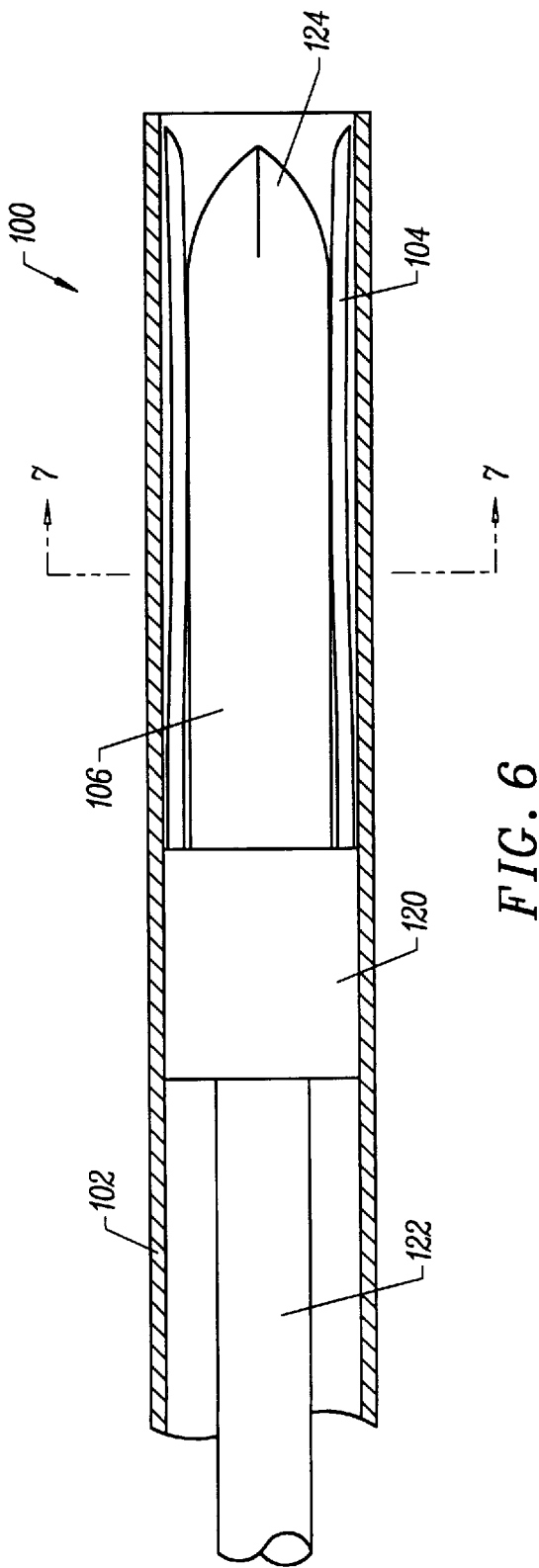
FIG. 6 is a cross-sectional view of a probe system constructed in accordance with the principles of the present invention.
Figure 8:
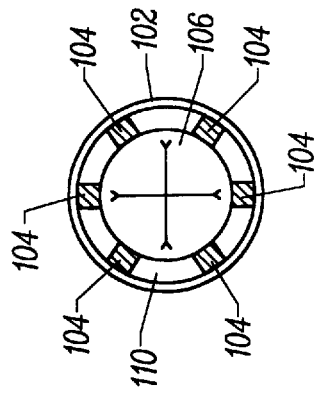
FIG. 8 is an end view of the distal end of the probe system of FIG. 6.
Figure 7:
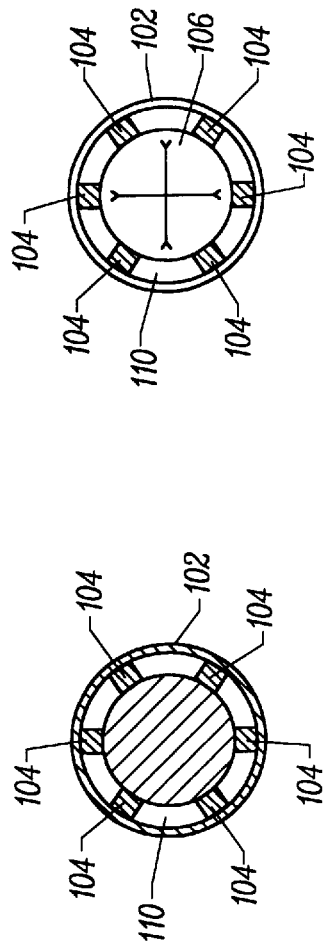
FIG. 7 is a cross-sectional view taken along line 7—7 of FIG. 6.

Referring now to FIG. 6–8, a first embodiment of a probe system 100 constructed in accordance with the principles of the present invention will be described. The probe system 100 includes a cannula 102 and a plurality of individual electrodes 104 constrained within the cannula over the outer cylindrical surface of a core member 106. The cannula 102 is only partly illustrated with a proximal length broken-off. The entire cannula will typically have a length in the range from about 5 cm to 30 cm, preferably from 10 cm to 20 cm, and outer diameter in the range from 1 mm to 5 mm, preferably from 1.3 mm to 4 mm, and an inner diameter in the range from 0.7 mm to 4 mm, preferably from 1 mm to 3.5 mm. The cannula may be formed from metals, plastics, or the like, and may be electrically active or inactive within the probe system, depending on the manner in which electrical energy is to be applied.

The individual electrodes 104 are illustrated as having rectangular cross-sectional geometries, with preferred dimensions generally within the ranges set forth above. The electrodes 104 are resilient and have a spring memory which causes them to curve along an arcuate path as they are distally extended from the cannula 102, as shown in FIGS. 13–16 hereinafter.

An annular envelope 110 is defined between the inner surface of the cannula 102 and the outer surface of core member 110, as best seen in FIGS. 7 and 8. The width of the annular envelope 110 (defined by the distance between the outer surface of core 106 and inner surface of cannula 102) as typically in the range from 0.1 mm to 1 mm, preferably from 0.15 mm to 0.5 mm, and will usually be selected to be slightly larger than the thickness of the individual electrodes 104 in the radial direction. In this way, the electrodes are constrained and held in generally axially aligned positions within the cannula 102. It will be appreciated that any misalignment can be observed from the distal end of the probe assembly, as shown in FIG. 8. To the extent that the individual distal ends of electrodes 104 may be non-evenly spaced-apart, a user or manufacturer can manually or otherwise realign the distal ends of the electrodes. Such realigned electrodes will then be maintained in proper alignment as the electrodes are constrained within the annular envelope.

Electrodes 104 are connected at their proximal ends to a cylindrical block 120 which in turn is secured to the distal end of a reciprocatable shaft 122. The core 106 is also secured to the distal end of cylindrical block 120 so that the core and electrodes move together as the shaft 122 is advanced distally or retracted proximally relative to the cannula 102. As the core 106 moves with the electrodes, it will be appreciated that the core will enter the tissue at the same time as the electrodes 104. Thus, the core 106 is shown to have a sharpened distal end 124 to enhance tissue penetration. The core 106 may be electrically coupled to the electrodes 104 (in which case it acts as an additional electrode of the same polarity as electrodes 104) or may be electrically isolated from the electrodes. When the core is electrically isolated, it can remain neutral during a treatment protocol, or alternatively it may be energized in the opposite polarity and thus act as a return electrode in a bipolar treatment protocol. A treatment protocol employing the probe system 100 is illustrated and described in detail in connection with FIGS. 13–16 hereinafter.

Note that a total of six electrodes are illustrated. Additional electrodes could be added in the spaces between the illustrated electrodes, with the maximum number of electrodes determined by the electrode width and total circumferential distance available (i.e., the electrodes could be tightly packed). It would also be possible to add additional concentric layers of electrodes, although such a design will generally not be preferred.

Figure 9:
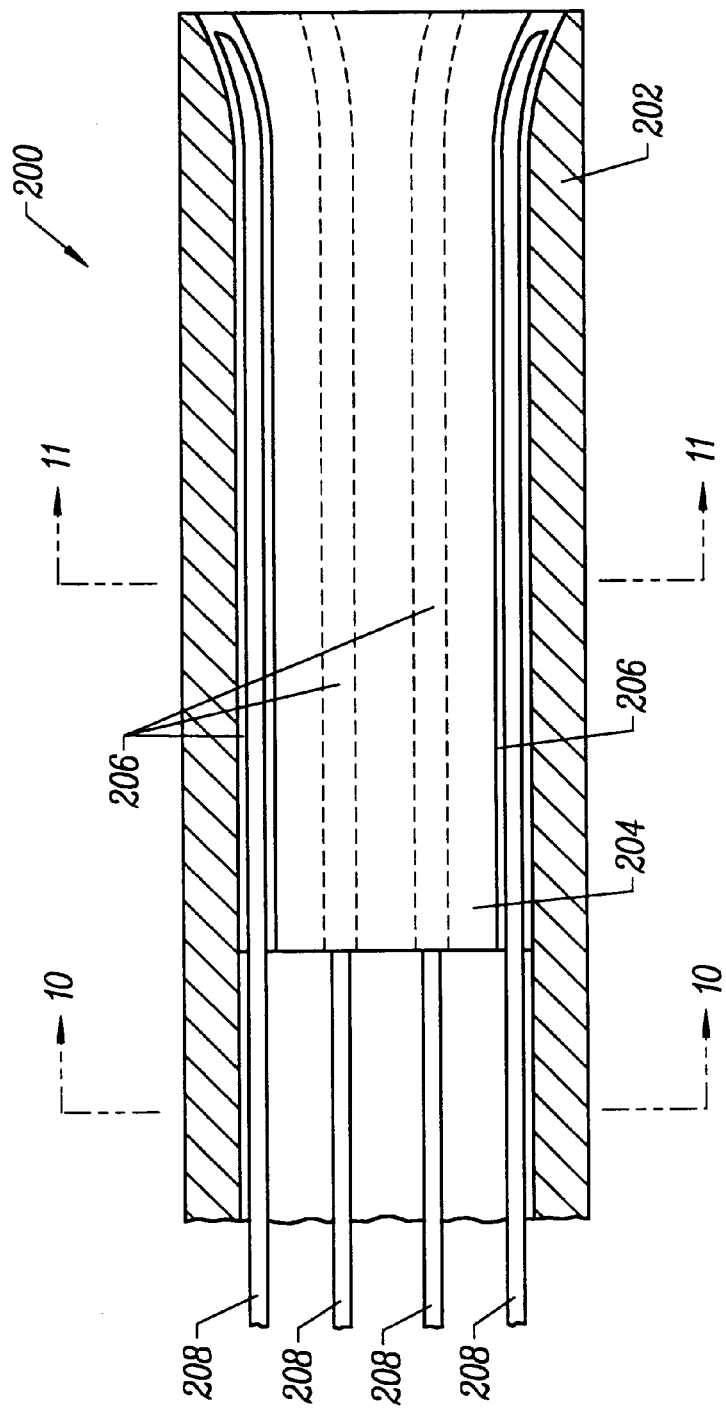
FIG. 9 illustrates a second embodiment of a probe system constructed in accordance with the principles of the present invention.
Figure 12:
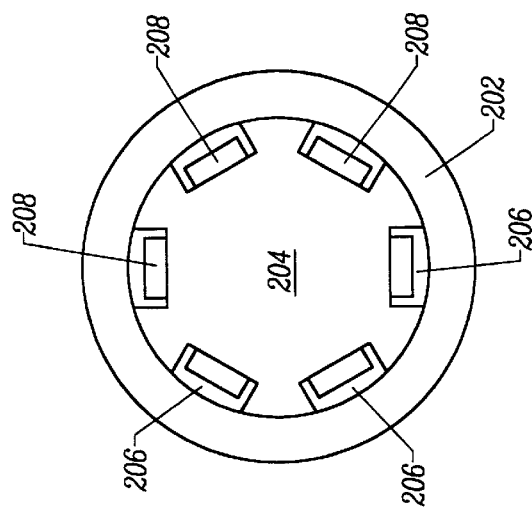
FIG. 12 is a distal end view of the probe system of FIG. 9.
Figure 11:
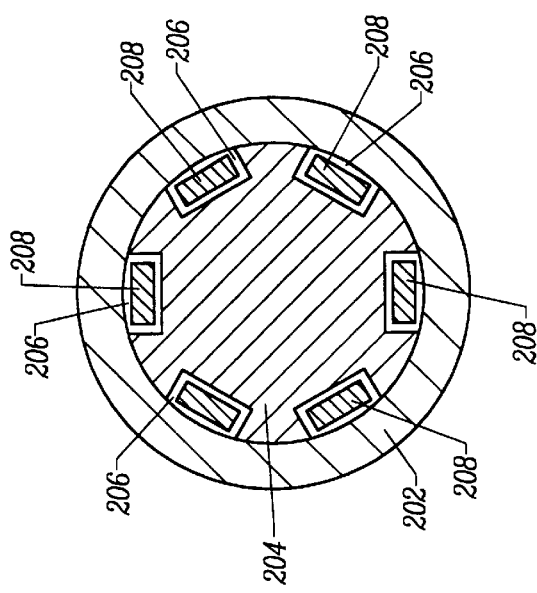
FIG. 11 is a cross-sectional view taken along line 11—11 of FIG. 9.
Figure 10:
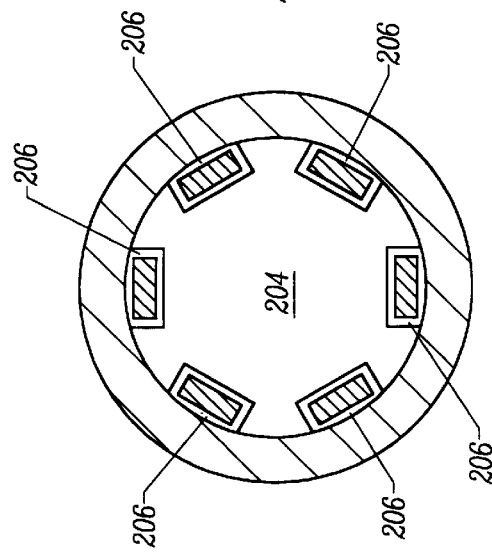
FIG. 10 is a cross-sectional view taken along line 10—10 of FIG. 9.

Referring now to FIGS. 9–12, a second exemplary embodiment of probe system 200 constructed in accordance with the principles of the present invention will be described. The probe system 200 comprises a cannula 202 having a core member 204 fixedly secured within a distal portion of the cannula. The core member 204 includes a plurality of circumferentially spaced-apart channels 206, each of which receives an individual electrode 208. The core 204 and cannula 202 thus define an annular envelope which is further constrained by the sidewalls of channels 206. Optionally, the distal ends of the channels may be straight or slightly flared radially outwardly, as best seen in FIG. 9. The electrodes 204 have spring memory causing them to assume an arcuate configuration and deflect radially outwardly as the electrodes are advanced distally relative to the cannula 202 and core 204. Preferably, the individual electrodes 204 have an asymmetric cross-sectional geometry, e.g. being rectangular, as illustrated in FIGS. 10–12.

Figure 12A:
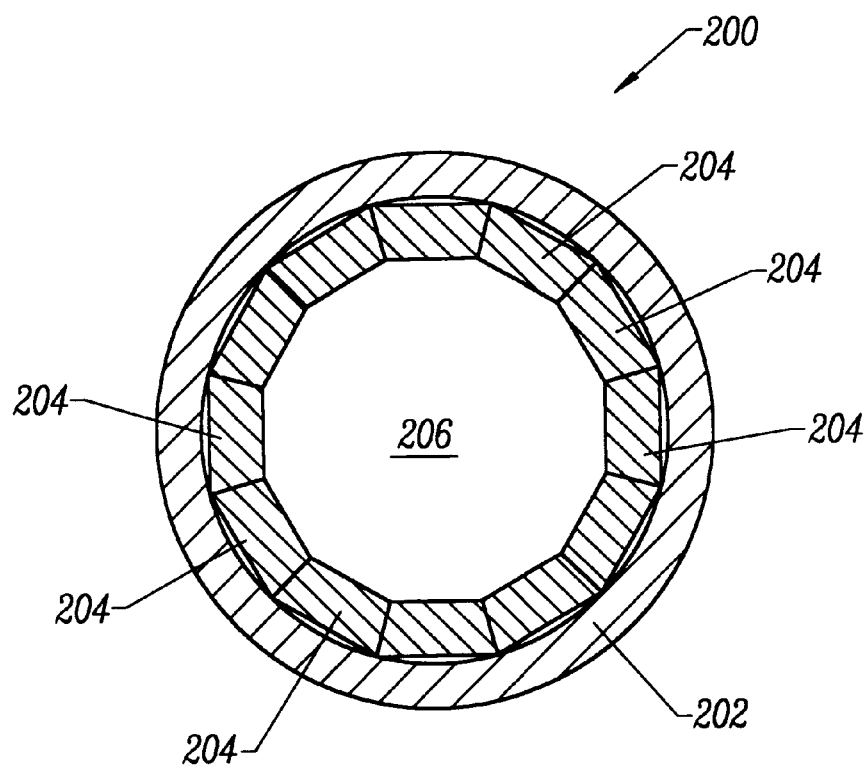
FIG. 12A is a cross-sectional view of an alternative embodiment of a probe system constructed in accordance with the principles of the present invention.

FIG. 12A illustrates an alternative probe assembly 200 comprising cannula 202 and a plurality of electrodes 204. FIG. 12A is a cross-sectional view of the probe assembly 200, and the electrodes 204 will typically be joined together near a proximal end of the cannula 202, although such a junction is not illustrated. Substantially equal spacing of the electrodes within an annular region within central lumen 206 of the cannula 202 is provided by nesting of the electrodes. Nesting is achieved by providing electrodes having dimensions sufficient to span the entire periphery of the cannula lumen when the electrodes are retracted therein. Preferably, the electrodes will be asymmetric, more preferably having rectangular or trapezoidal cross-sections, with the trapezoidal cross-section being illustrated. Such a nested electrode configuration will be most useful with electrode arrays including at least four individual electrodes, usually including at least eight individual electrodes, and preferably having ten electrodes, twelve electrodes, or more. The nested electrode configuration of FIG. 12A can be combined with the central core embodiment of the present invention, as described above. Optionally, the central core may extend over only a proximal portion of the cannula and electrode assembly, where the interior space between the electrodes and the distal portion of the assembly is left empty. The empty distal space is advantageous since it helps avoid jamming of the electrodes as they are drawn back into the cannula after use in tissue. Without the central space, the tissue can become jammed between the electrodes, making retraction more difficult.

Figure 13:
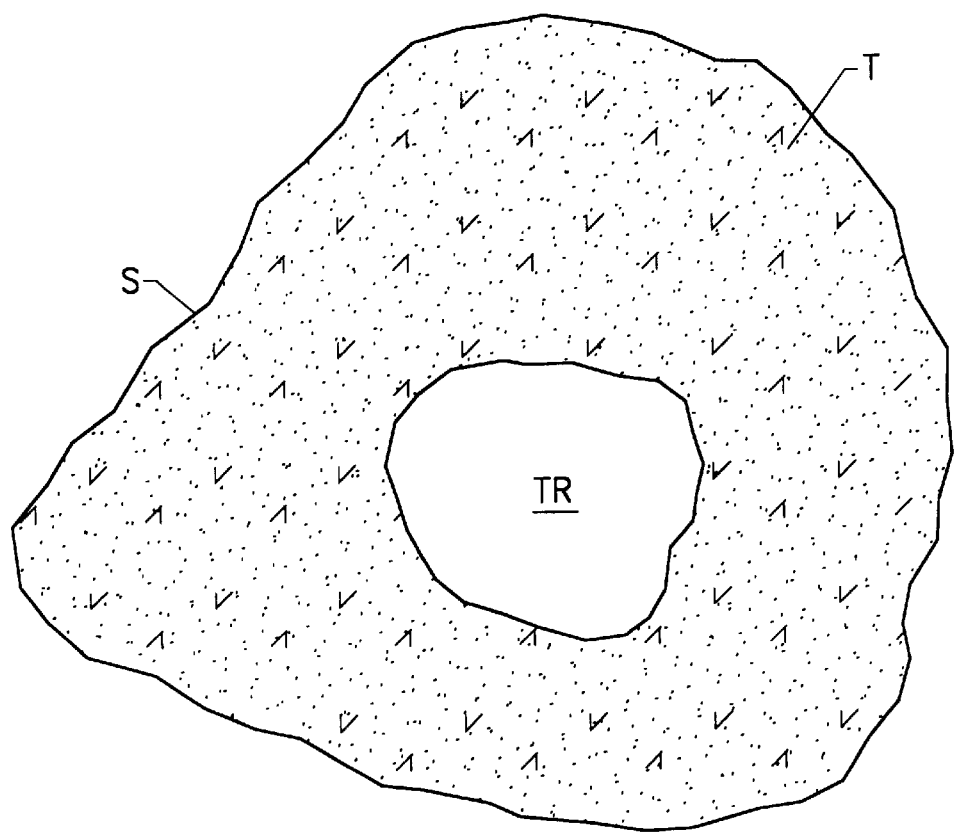
FIGS. 13–16 illustrate use of the probe of FIG. 6 entreating a tissue target region according to the method of the present invention.

Referring now to FIGS. 13–16, a treatment region T within tissue T is located beneath the skin or an organ surface S of a patient. The treatment region T may be a solid tumor or other lesion where it is desired to treat the tissue by RF hyperthermia. The treatment region T prior to treatment is shown in FIG. 13.

Figure 14:
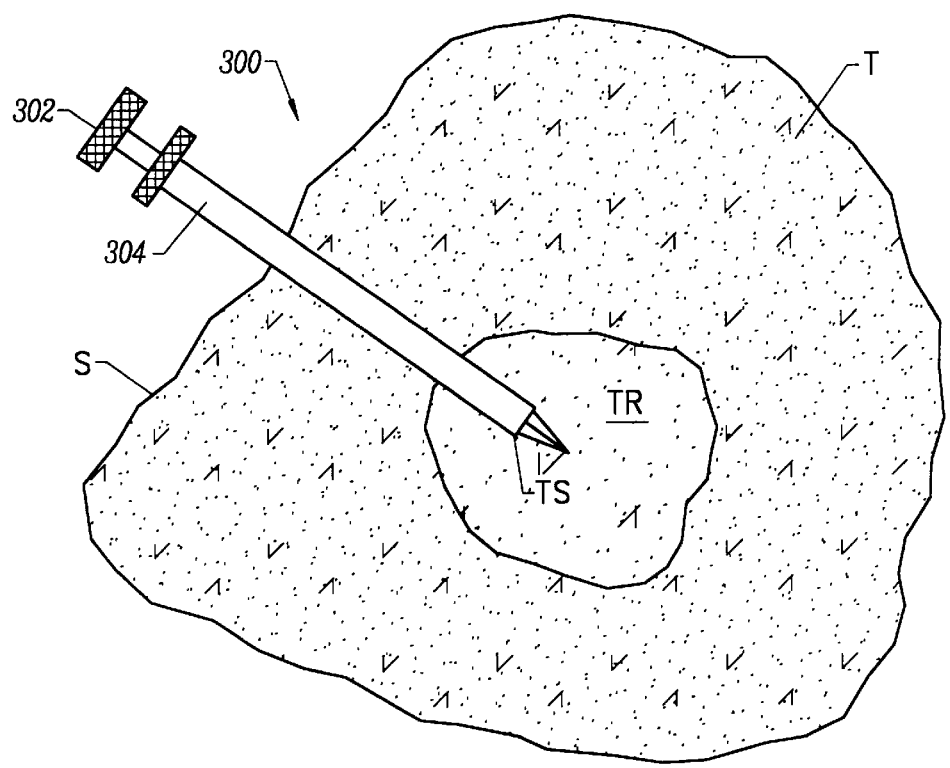
Figure 15:
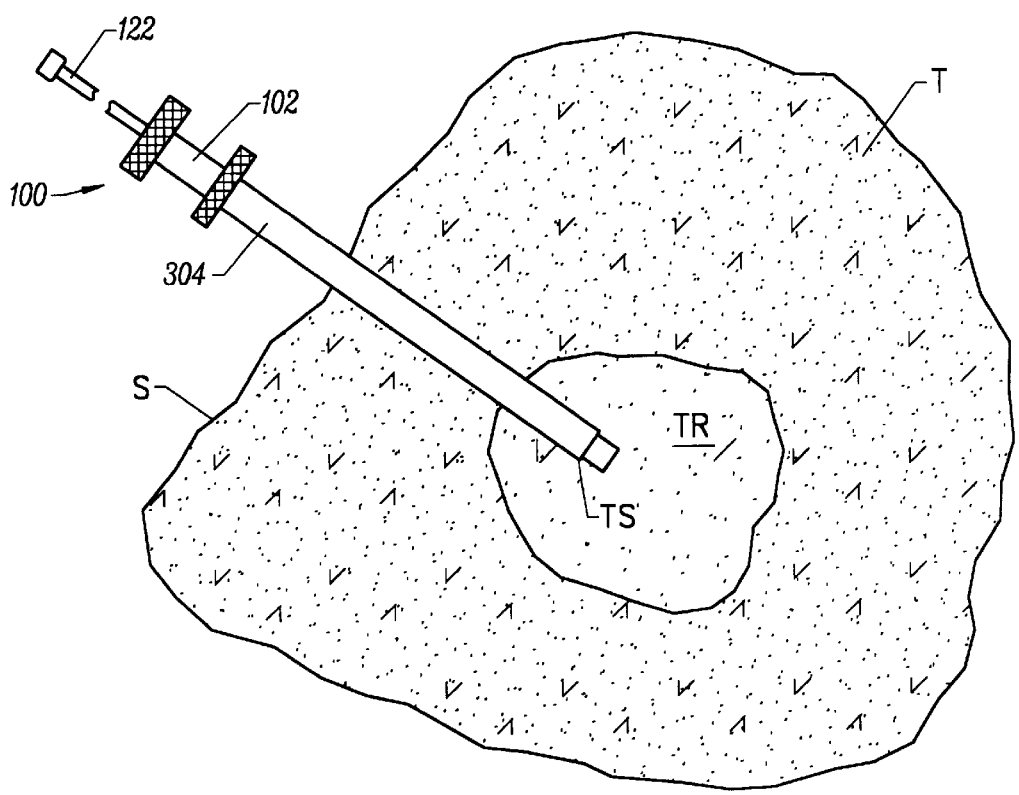

In order to introduce an electrode array according to the method of the present invention, a conventional sheath and obturator/stylet assembly 300 is introduced through the skin or organ surface S so that a distal end of the sheath lies at or within a target site TS within the treatment region, as shown in FIG. 14. In many cases, the sheath and obturator/stylet assembly 300 may be introduced percutaneously directly through the patient's skin. In other cases, however, it may be desirable to provide an open surgical incision or to place a trocar through the skin in order to introduce the stylet to the organ surface S. In either case, the obturator/stylet 302 is then removed from the sheath 304, leaving the sheath in place as shown in FIG. 15. The cannula 102 of probe system 100 may then be introduced through the lumen of sheath 304 so that a distal end advances from the sheath into the target region T, also as shown in FIG. 15.

Figure 16:
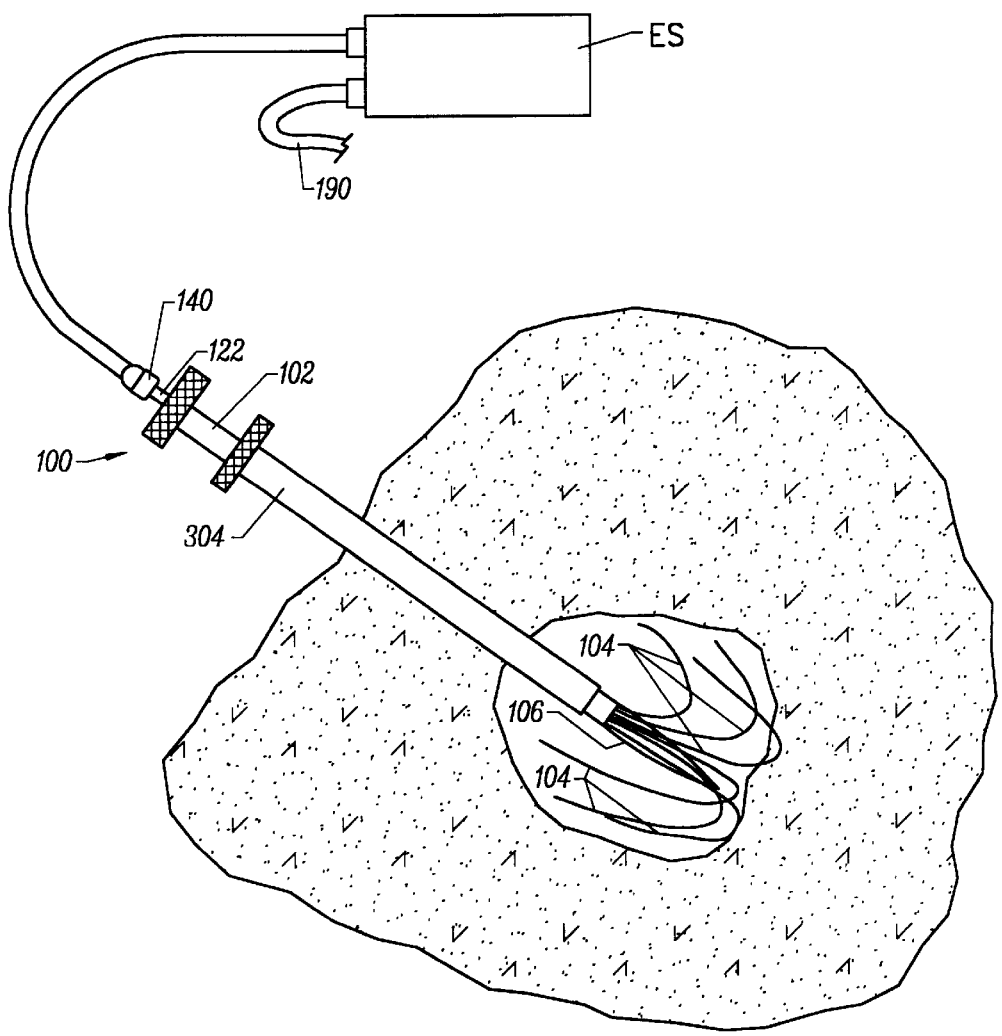

After the cannula 102 is properly placed, the shaft 122 will be distally advanced to deploy the electrodes 104 radially outwardly from the distal end of the cannula, as shown in FIG. 16. The shaft 122 will be advanced sufficiently so that the electrodes 104 fully evert in order to circumscribe substantially the entire treatment region TR. The core member 106 also advances distally into the tissue along a line which is axially aligned with the cannula 102.

A connector 140 at the proximal end of shaft 122 may then be connected to an electrosurgical power supply ES. Suitable power supplies are available from commercial suppliers as listed above. A second connecting cable 190 extends from the electrosurgical power supply ES to a dispersive plate electrode (not shown) on the patient for monopolar operation.

Although the foregoing invention has been described in some detail by way of illustration and example, for purposes of clarity of understanding, it will be obvious that certain changes and modifications may be practiced within the scope of the appended claims.

What is claimed is:

1. A probe system for penetrating a plurality of electrodes into tissue, said probe system comprising:
   a cannula having a proximal end, a distal end, and a lumen extending to at least the distal end,
   a core disposed coaxially within the cannula lumen, said core having a cylindrical outer surface which together with an inner surface of the cannula lumen defines an annular envelope; and
   a plurality of resilient electrodes disposed in the annular envelope wherein at least a portion of the electrodes are mechanically coupled to the core to reciprocate between a proximally retracted position wherein all electrodes are radially constrained within the lumen and a distally extended position wherein all electrodes deploy radially outwardly, said plurality including at least three electrodes,
   whereby the envelope maintains substantially equal circumferential spacing between adjacent electrodes when retracted in the cannula lumen.

2. A probe system as in claim 1, wherein the core has a sharpened distal end to facilitate penetration into tissue.

3. A probe system as in claim 1, wherein the core is electrically coupled to the electrodes.

4. A probe system as in claim 1, wherein the core is electrically isolated from the electrodes.

5. A probe system as in claim 1, wherein at least one of the outer cylindrical surface of the core and the inner surface of the cannula lumen has channels formed therein for receiving and aligning the electrodes.

6. A probe system as in claim 1, wherein the annular envelope has a width in a radial direction which is less than or equal to a distance twice that of the thickness of an electrode.

7. A probe system as in claim 1, wherein at least some of the electrodes are shaped so that they assume an outwardly everted configuration as they are extended distally into tissue from the distal end of the cannula.

8. A probe system as in claim 1, further comprising a stylet reciprocatably received in the cannula lumen, wherein the stylet may be used for initially positioning the cannula in tissue and thereafter exchanged with the electrodes.

9. A probe system as in claim 1, wherein the cannula has a length in the range from 5 cm to 30 cm and an outer diameter in the range from 1 mm to 5 mm.

10. A probe system as in claim 1, wherein the electrodes deploy outwardly to a radius in the range from 0.5 cm to 3 cm when fully distally extended from the cannula.

11. A probe system as in claim 1, wherein the plurality includes at least five electrodes.

12. A probe system as in claim 1, wherein the plurality includes at least eight electrodes.

13. A probe system as in claim 1, wherein the plurality includes at least ten electrodes.

14. A probe system for penetrating a plurality of electrodes into tissue, said probe system comprising:
   a cannula having a proximal end, a distal end, and a lumen extending to at least the distal end; and
   a plurality of resilient electrodes, at least a portion having asymmetric cross-sections with a major dimension aligned circumferentially and a minor dimension aligned radially, disposed in the cannula lumen to reciprocate between a proximally retracted position wherein all electrodes are radially constrained within the lumen and a distally extended position wherein all electrodes deploy radially outwardly, said plurality including at least three electrodes,
   whereby the shape and alignment of the electrodes maintains substantially equal circumferential spacing between adjacent electrodes when retracted in the cannula lumen.

15. A probe system as in claim 14, wherein the major dimension is at least 50% larger than the minor dimension.

16. A probe system as in claim 15, wherein the electrodes have a rectangular cross-section.

17. A probe system as in claim 14, wherein the electrodes are nested together in a close packed configuration within an annular ring.

18. A probe system as in claim 14, wherein at least some of the electrodes are shaped so that they assume an outwardly everted configuration as they are extended distally into tissue from the distal end of the cannula.

19. A probe system as in claim 14, further comprising a stylet reciprocatably received in the cannula lumen, wherein the stylet may be used for initially positioning the cannula in tissue and thereafter exchanged with the electrodes.

20. A probe system as in claim 14, wherein the cannula has a length in the range from 5 cm to 30 cm and an outer diameter in the range from 1 mm to 5 mm.

21. A probe system as in claim 14, wherein the electrodes deploy outwardly to a radius in the range from 0.5 cm to 3 cm when fully distally extended from the cannula.

22. A probe system as in claim 14, wherein the plurality includes at least five electrodes.

23. A probe system as in claim 14, wherein the plurality includes at least eight electrodes.

24. A probe system as in claim 14, wherein the plurality includes at least ten electrodes.

25. A probe system comprising:
   a cannula having a proximal end, a distal end, and a lumen extending to at least the distal end,
   a cylindrical core disposed coaxially within the cannula lumen to define an annular envelope; and
   a plurality of resilient electrodes disposed in the annular envelope to reciprocate between a proximally retracted position wherein all electrodes are radially constrained within the envelope and a distally extended position wherein all electrodes deploy radially outwardly, at least a portion of said electrodes having asymmetric cross-sections with a major dimension aligned circumferentially within the annular envelope and a minor dimension aligned radially within the annular envelope.

26. A probe system as in claim 25, wherein the core is mechanically coupled to and reciprocates with the electrodes.

27. A probe system as in claim 26, wherein the core has a sharpened distal end to facilitate penetration into tissue.

28. A probe system as in claim 25, wherein the core is electrically coupled to the electrodes.

29. A probe system as in claim 25, wherein the core is electrically isolated from the electrodes.

30. A probe system as in claim 25, wherein the core is mechanically coupled to the cannula so that the electrodes translate past the surface of the core as the electrodes are advanced distally from the cannula.

31. A probe system as in claim 25, wherein at least one of the outer cylindrical surface of the core and the inner surface of the cannula lumen has channels formed therein for receiving and aligning the electrodes.

32. A probe system as in claim 25, wherein the annular envelope has a width in a radial direction which is less than or equal to a distance twice that of the thickness of an electrode.

33. A probe system as in claim 25, wherein the major dimension of the electrode cross-section is at least 50% larger than the minor dimension.

34. A probe system as in claim 33, wherein the electrodes have a rectangular or trapezoidal cross-section.

35. A probe system as in claim 25, wherein at least some of the electrodes are shaped so that they assume an outwardly everted configuration as they are extended distally into tissue from the distal end of the cannula.

36. A probe system as in claim 25, further comprising a stylet reciprocatably received in the cannula lumen, wherein the stylet may be used for initially positioning the cannula in tissue and thereafter exchanged with the electrodes.

37. A probe system as in claim 25, wherein the cannula has a length in the range from 5 cm to 30 cm and an outer diameter in the range from 1 mm to 5 mm.

38. A probe system as in claim 25, wherein the electrodes deploy outwardly to a radius in the range from 0.5 cm to 3 cm when fully distally extended from the cannula.

39. A probe system as in claim 25, wherein the plurality includes at least three electrodes.

40. A probe system as in claim 25, wherein the plurality includes at least five electrodes.

41. A probe system as in claim 25, wherein the plurality includes at least eight electrodes.

42. A probe system as in claim 25, wherein the plurality includes at least ten electrodes.

43. A probe system comprising:
a cannula having a proximal end, a distal end, and a lumen extending to at least the distal end; and
at least four electrodes reciprocatably disposed within the lumen of the cannula, wherein the electrodes are nested within an annulus within the cannula lumen when retracted therein, each said electrode having an asymmetric cross-section.

44. A probe system as in claim 43, including at least eight electrodes.

45. A probe system as in claim 43, wherein the annulus is constrained to have a width in a radial direction which is less than or equal to a distance twice that of the thickness of an electrode.

46. A probe system as in claim 43, wherein the asymmetric cross-sections are rectangular or trapezoidal.

47. A probe system as in claim 43, wherein at least some of the electrodes are shaped so that they assume an outwardly everted configuration as they are extended distally into tissue from the distal end of the cannula.

48. A probe system as in claim 43, wherein the cannula has a length in the range from 5 cm to 30 cm and an outer diameter in the range from 1 mm to 5 mm.

49. A probe system as in claim 43, wherein the electrodes deploy outwardly to a radius in the range from 0.5 cm to 3 cm when fully distally extended from the cannula.

50. A method for delivering current to a target region within solid tissue comprising:
constraining a plurality of at least three electrodes within a cannula, wherein at least a portion of the electrodes have an asymmetrical cross-section and a distal tip arranged in a pattern whereby the distal tips are substantially equally spaced-apart within an annular region near a distal end of the cannula,
advancing the electrodes distally from the cannula into tissue at the target region, wherein the electrodes deploy radially outwardly in a symmetric pattern into the tissue; and
applying electrical current to the tissue through the electrodes.

51. A method as in claim 49, wherein the electrode distal tips are disposed in an annular region defined between an outer cylindrical surface of a core member disposed in the cannula and an inner cylindrical surface of a lumen of the cannula, wherein the distance between said outer cylindrical surface and said inner cylindrical surface is no more than twice that of the thickness of an electrode.

52. A method in claim 50, wherein a cannula lumen reciprocatably receives a core, said core having a cylindrical outer surface which together with the inner surface of the cannula lumen defines the annular region.

53. A method as in claim 52, wherein the core advances into the tissue together with the electrodes.

54. A method as in claim 52, wherein the electrodes advance past the core which remains immobile relative to the cannula.

55. A method as in claim 50, wherein the asymmetric cross-sections have a major dimension aligned circumferentially to maintain axial alignment of the electrodes and minor dimension aligned radially, where the electrodes are shaped to bend about an axis parallel to the minor dimension as the electrodes are advanced distally from the cannula.

56. A method as in claim 50, wherein the tips of the electrodes are nested within an annulus near the distal end of the cannula lumen prior to advancement.

57. A method as in claim 50, wherein the current is radio frequency current.

58. A method as in claim 50, wherein the electrodes are attached to one pole of a current source and a dispersive electrode is attached to another pole of the current source.

59. A method as in claim 50, wherein some of the electrodes are attached to one pole of a current source and others of the electrodes are attached to another pole of the current source to deliver current in a bipolar manner.

60. A method for deploying electrodes in tissue, said method comprising:
providing a plurality of at least three asymmetric electrodes constrained within a cannula; and
advancing each of the electrodes distally from the cannula into tissue, wherein spacing between adjacent electrodes is maintained within ±20% of the average distance between electrodes as the electrodes are advanced.

61. A method as in claim 60, wherein the spacing is maintained to within ±10% of the average distance.

62. A method as in claim 60, wherein the spacing is maintained to within ±5% of the average distance.

63. A method as in claim 60, wherein the spacing is further maintained by a central core within the cannula.

64. A method as in claim 60, wherein the spacing is further maintained by providing the electrodes in a nested configuration.

65. A method as in claim 60, further comprising applying a cutting RF current to the electrodes as they are advanced.

66. A method as in claim 65, further comprising applying an ablating RF current to the electrodes after they are advanced.

* * * * *